United States Patent

Abbott et al.

[11] 4,116,871
[45] Sep. 26, 1978

[54] PREPARATION OF PHOSPHORUS-CONTAINING ACIDS AND SALTS

[75] Inventors: Andrew Doyle Abbott, Greenbrae; George J. Benoit, San Anselmo, both of Calif.

[73] Assignee: Chevron Research Company, San Francisco, Calif.

[21] Appl. No.: 811,228

[22] Filed: Jun. 29, 1977

[51] Int. Cl.² .................. C10M 1/48; C10M 3/42; C10M 5/24; C10M 7/46
[52] U.S. Cl. .................. 252/32.7 E; 252/46.6; 252/400 A; 424/224
[58] Field of Search .............. 252/32.7 E, 400 A, 46.6

[56] References Cited

U.S. PATENT DOCUMENTS

| | | | |
|---|---|---|---|
| 2,526,497 | 10/1950 | Mikeska | 252/46.6 |
| 2,565,920 | 8/1951 | Hook et al. | 252/46.6 |
| 2,838,555 | 6/1958 | Goldsmith | 252/32.7 E |
| 3,004,916 | 10/1961 | Ertelt | 252/32.7 E |
| 3,423,316 | 1/1969 | Dickert et al. | 252/32.7 E |
| 3,595,792 | 7/1971 | Elliott et al. | 252/32.7 E |
| 3,742,099 | 6/1973 | Colclough et al. | 252/32.7 E |

*Primary Examiner*—Irving Vaughn
*Attorney, Agent, or Firm*—D. A. Newell; C. J. Tonkin; L. L. Vaughan

[57] ABSTRACT

Phosphorus-containing acids and salts are prepared by heating a mixture of (A) an acid of the formula

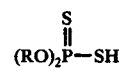

where R is alkyl, with (B) an acid of the formula

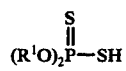

where R¹ is aryl, for 3 to 10 hours at 55° to 95° C to form a mixture of acids (A) and (B) and an acid of the formula

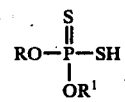 (C)

and optionally neutralizing to a salt to be used in lubricating oil.

7 Claims, No Drawings

PREPARATION OF PHOSPHORUS-CONTAINING ACIDS AND SALTS

BACKGROUND OF THE INVENTION

This invention relates to a new method for preparing certain phosphorus-containing acids and salts.

The use of dialkyldithiophosphates and diaryldithiophosphates as additives in lubricating oils is well known. The diaryldithiophosphates have better thermal stability compared to the dialkyldithiophosphates. However, the dialkydithiophosphates have better extreme-pressure and hydrolytic stability compared to the diaryldithiophosphates.

The preparation of mixed aryl-alkyl dithiophosphates by methods previously known in the art is very difficult. For example, if a mixture of an alcohol and an aromatic phenol is reacted directly with phosphorus pentasulfide, the differences in the reactivity of the aromatic and alkyl alcohols results in the formation of very little of the mixed aryl-alkyl dithiophosphoric acid. If the salts (e.g., Zn salts) of the aryl dithiophosphate and the alkyl dithiophosphate are mixed, equilibration to a mixed aryl-alkyl dithiophosphate salt does not occur.

DESCRIPTION OF THE PRIOR ART

U.S. Pat. No. 3,004,916 discloses metal dihydrocarbyl dithiophosphates, and specially names a compound in which one of the hydrocarbyl groups is alkyl and one is naphthyl. However, the preparation or a specific example of the use of such a compound is not taught.

U.S. Pat. No. 3,493,507 teaches a grease composition comprising a metal monoalkyl/monoarylthiophosphate. However, no example or discussion of the preparation of such a thiophosphate is included in the patent.

U.S. Pat. No. 2,526,497 teaches an additive prepared by reacting $P_2S_5$ with a mixture of a wax phenol and an aliphatic alcohol.

U.S. Pat. No. 2,565,920 teaches intermediate O,O-diesters of dithiophosphoric acids which include mixed alkyl and phenyl radicals.

SUMMARY OF THE INVENTION

Phosphorus-containing acids and salts are prepared by heating a mixture of (A) an acid of the formula

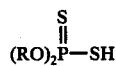

where R is alkyl, with (B) an acid of the formula

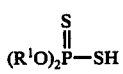

where $R^1$ is aryl, for 3 to 10 hours at 55° to 95° C to form a mixture of acids (A) and (B) and an acid of the formula

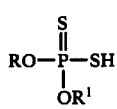 (C)

and optionally neutralizing to a salt.

By "alkyl" is meant any primary or secondary alkyl group, preferably of 1 to 20 carbon atoms. By "aryl" is meant any aromatic hydrocarbon group, preferably phenyl or phenyl substituted by 1 to 3 alkyl groups of 1 to 20 carbon atoms each.

The dithiophosphoric acids that are formed using the process of this invention can be neutralized with a compound which supplies either monovalent or divalent cations. By "monovalent cation" (M) is meant a cation having a valency of $+1$. Typical monovalent cations include ammonium, $R''_4N^+$ where $R''$ is hydrogen or hydrocarbyl, especially alkyl or aryl, $Na^+$, $K^+$, $Li^+$, and the like. By "divalent cation" ($M^1$) is meant a cation of $+2$ valency. Typical cations included in this group are $Ca^{++}$, $Ba^{++}$, $Mg^{++}$, $Zn^{++}$, $Sn^{++}$, $Pb^{++}$, $Cd^{++}$ and $Ni^{++}$ cations.

As is understood by one skilled in the art, when a divalent salt is formed from a mixture of acids, the resultant salt each anion can be the same, i.e., each contributed by an acid of type A, B or C, or different, e.g., one anion from acid A and one from acid C; one anion from acid B and one from acid C; etc.

The neutralization step involves the reaction of the dithiophosphoric acid with a compound supplying the cations to yield a salt. This type of reaction is well known in the art. Typical compounds which are used to provide the monovalent or divalent cation as a result of the direct neutralization of the dithiophosphoric acid include sodium hydroxide, potassium hydroxide, calcium oxide, zinc, zinc oxide, zinc carbonate, lead acetate, lead nitrate, and the like. An alternative, less preferred method for forming those compounds containing a divalent cation, $M^1$, is to first prepare a salt with a monovalent cation, such as a sodium dithiophosphate, and then prepare the divalent cation salt by metathesis. Using a metathesis procedure, the monovalent salt, such as the sodium or potassium salt, can be partially purified and then combined with the divalent-cation-supplying compound, such as a Group II metal chloride or lead acetate or lead nitrate, in a suitable solvent system. The reaction mixture is stirred for a long-enough time to allow metathesis to occur. Then the phase containing the byproduct salt is removed and solvent may be evaporated as desired. The alkyl-aryl dithiophosphoric acids may be reacted with olefins, alkylene oxides, etc., by methods known in the art to form the corresponding esters.

The reaction of this invention is carried out at a temperature of from 35° to 105° C, preferably 55° to 95° C. While the reaction is normally carried out at atmospheric pressure, pressures above or below atmospheric may be used, if desired. The reaction to form the mixed dithiophosphoric acids of this invention usually proceeds to completion within from 3 to 10 hours. The reaction between the two starting dithiophosphoric acids, $(RO)_2P(S)SH$ and $(R^1O)_2P(S)SH$, may be carried out neat or in the presence of a solvent, e.g., any hydrocarbon solvent having a suitable boiling range. The products, mixed arylalkyldithiophosphoric acids or the salts thereof, may, if desired, be purified by any conventional methods known in the art.

The compounds of this invention are primarily useful as additives for lubricating oils; however, they may also find utility in other fields such as, for example, insecticides, plasticizers, and oxidation inhibitors.

The compositions of this invention for use as lubricating oil additives can be used in lubricating oil compositions from synthetic or petroleum-derived lubricating oils. These oils can be paraffinic, naphthenic, halo-substituted hydrocarbon, synthetic esters, or combinations thereof. Generally, the oils have viscosities in the range of 35 to 50,000 Saybolt Universal Seconds (SUS) at 100° F (38° C).

An effective amount of the dithiophosphate of this invention which would provide desired antiwear properties as well as the antioxidant properties in lubricating oil formulations can vary widely with the particular dithiophosphate that is being used and the particular type of environment in which it is used. However, generally from about 0.03 to 0.15 weight percent phosphorus derived from a dithiophospate, and more usually from about 0.06 to 0.10 weight percent phosphorus, is present in the lubricating oil compositions.

Lubricating oil additive compositions and concentrates can be prepared from the dithiophosphate mixture and usually comprise from about 99 to 1 weight percent of a diluent, usually an oil of lubricating viscosity, and from about 1 to 99 weight percent of the dithiophosphate. Lubricating oil compositions may contain as little as 0.1% weight zinc alkyl aryl dithiophosphate. Certain concentrates could, of course, contain additional additives, thereby proportionally reducing the amount of oil present. Concentrates contain as much of the dithiophosphate as is practical, since the concentrates are prepared to reduce shipping costs, requirements, and so forth. Typically the concentrates contain sufficient diluent to make them easy to handle during shipping and storage. Usually the diluent is inert and preferably is an oil of lubricating viscosity, so that the concentrate may be readily mixed with the lubricating oil to prepare the lubricating oil composition.

EXAMPLES

The following example is included to further illustrate the mixed alkylaryldithiophosphoric acids and salts of this invention.

EXAMPLE 1

(A) A mixture of 17,070 g $(R^1O)_2P(S)SH$, where $R_1$ is the phenyl alkylated by propylene tetramer, having an acid number of 89.45 mg KOH/g, and 7920 g dialkyldithiophosphoric acid, made from mixed primary $C_4$ and $C_6$ alcohols, having an acid number of 192.8 mg KOH/g, was heated to 66° C and held at that temperature for 6.5 hours. The acid number of the mixture was calculated to be 122.2 mg KOH/g. At the end of this time, the acid number of the product was 122.5 mg KOH/g, showing that no change in overall acid number occurred. As determined by $P_{31}$ NMR, the distribution of product was 23 mol percent di(alkylphenyl) dithiophosphoric acid, 50 mol percent dialkyldithiophosphoric acid, and 27 mol percent alkylphenyl alkyl dithiophosphoric acid.

(B) To 5.0 kg neutral diluent oil and 6.5 kg naphtha was added 2.4 kg zinc oxide. The mixture was heated to 43° C, and 20 kg of the product of Part (A) was added over an 8-minute time period. The temperature of the reaction mixture increased to 55.6° C and was held there for 1 hour. The reaction mixture was filtered through diatomaceous earth. The filtrate was stripped to 107° C at 23 mm Hg for 20 minutes. The product contained 5.0% P, 5.15% Zn and 10.5% S. As determined by $P_{31}$ NMR, the product corresponds to the following distribution: 29 mol percent zinc di(alkylphenyl)dithiophosphate, 44 mol percent zinc dialkyldithiophosphate, and 27 mol percent zinc alkylphenyl alkyl dithiophosphate.

What is claimed is:

1. A process which comprises heating a mixture of an acid of the formula

and an acid of the formula

for 3 to 10 hours at 55° to 95° C to form a mixture of acids (A) and (B) and an acid of the formula

wherein R is alkyl and $R^1$ is aryl.

2. The process according to claim 1 wherein the acid mixture is neutralized with a compound supplying a monovalent or divalent cation.

3. The process according to claim 2 wherein said compound is zinc, zinc oxide, zinc carbonate, potassium hydroxide or sodium hydroxide.

4. The process of claim 3 wherein R is $C_1$-$C_{20}$ is alkyl, $R^1$ is phenyl or phenyl substituted by 1-3 alkyl groups of 1-20 carbon atoms each, and said compound is zinc oxide or zinc carbonate.

5. A lubricating oil composition containing an oil of lubricating viscosity and from 0.1 to 99% by weight of the product prepared by the process of claim 4.

6. The product prepared by the process of claim 1.

7. The product prepared by the process of claim 4.

* * * * *